(12) United States Patent
Van Dross-Anderson et al.

(10) Patent No.: US 11,571,401 B2
(45) Date of Patent: Feb. 7, 2023

(54) COMPOUNDS, COMPOSITIONS, KITS, AND METHODS FOR ACTIVATING IMMUNE CELLS AND/OR AN IMMUNE SYSTEM RESPONSE

(71) Applicant: East Carolina University, Greenville, NC (US)

(72) Inventors: Rukiyah T. Van Dross-Anderson, Winterville, NC (US); Rene Escobedo, Wilson, NC (US)

(73) Assignee: East Carolina University, Greenville, NC (US)

(*) Notice: Subject to any disclaimer, the term of this patent is extended or adjusted under 35 U.S.C. 154(b) by 164 days.

(21) Appl. No.: 16/642,178

(22) PCT Filed: Aug. 30, 2018

(86) PCT No.: PCT/US2018/048806
§ 371 (c)(1),
(2) Date: Feb. 26, 2020

(87) PCT Pub. No.: WO2019/046556
PCT Pub. Date: Mar. 7, 2019

(65) Prior Publication Data
US 2020/0306212 A1 Oct. 1, 2020

Related U.S. Application Data

(60) Provisional application No. 62/553,510, filed on Sep. 1, 2017.

(51) Int. Cl.
*A61K 31/164* (2006.01)
*A61P 35/00* (2006.01)

(52) U.S. Cl.
CPC ............ *A61K 31/164* (2013.01); *A61P 35/00* (2018.01)

(58) Field of Classification Search
None
See application file for complete search history.

(56) References Cited

U.S. PATENT DOCUMENTS

| | | |
|---|---|---|
| 3,710,795 A | 1/1973 | Higuchi et al. |
| 3,817,837 A | 6/1974 | Rubenstein et al. |
| 3,927,193 A | 12/1975 | Hansen et al. |
| RE28,819 E | 5/1976 | Thompson |
| 4,044,126 A | 8/1977 | Cook et al. |
| 4,328,245 A | 5/1982 | Yu et al. |
| 4,331,647 A | 5/1982 | Goldenberg |
| 4,348,376 A | 9/1982 | Goldenberg |
| 4,358,603 A | 11/1982 | Yu |
| 4,361,544 A | 11/1982 | Goldenberg |
| 4,364,923 A | 12/1982 | Cook et al. |
| 4,374,925 A | 2/1983 | Litman et al. |
| 4,409,239 A | 10/1983 | Yu |
| 4,410,545 A | 10/1983 | Yu et al. |
| 4,414,209 A | 11/1983 | Cook et al. |
| 4,444,744 A | 4/1984 | Goldenberg |
| 4,468,457 A | 8/1984 | Goldenberg et al. |
| 4,474,893 A | 10/1984 | Reading |
| 4,479,895 A | 10/1984 | Auditore-Hargreaves |
| 4,522,811 A | 6/1985 | Eppstein et al. |
| 4,624,846 A | 11/1986 | Goldenberg |
| 4,818,709 A | 4/1989 | Primus et al. |
| 4,946,778 A | 8/1990 | Ladner et al. |
| 5,033,252 A | 7/1991 | Carter |
| 5,052,558 A | 10/1991 | Carter |
| 5,323,907 A | 6/1994 | Kalvelage |
| 5,709,874 A | 1/1998 | Hanson et al. |
| 5,759,542 A | 6/1998 | Gurewich |
| 5,840,674 A | 11/1998 | Yatvin et al. |
| 5,860,957 A | 1/1999 | Jacobsen et al. |

(Continued)

FOREIGN PATENT DOCUMENTS

| | | |
|---|---|---|
| EP | 0172963 A1 | 3/1986 |
| WO | 0212445 A1 | 2/2002 |
| WO | 2017151836 | 9/2017 |

OTHER PUBLICATIONS

Borch et al. "Reorienting the immune system in the treatment of cancer by using anti-PD-1 and anti-PD-L1 antibodies" Drug Discovery Today, 20(9):1127-1134 (2015).
Extended European Search Report corresponding to European Patent Application No. 18851816.1 (14 pages) (dated Apr. 20, 2021).
Ladin et al. "Synthesis and Evaluation of the Novel Prostamide, 15-Deoxy, Δ12,14-Prostamide J2, as a Selective Antitumor Therapeutic" Molecular Cancer Therapeutics, 16(5):838-849 (2017).
Patsos et al. "The endogenous cannabinoid, anandamide, induces cell death in colorectal carcinoma cells: a possible role for cyclooxygenase 2" Gut Microbiota, 54(12):1741-1750 (2005).
Elhassanny et al. "Damage-associated molecular pattern (DAMP) activation in melanoma: investigation of the immunogenic activity of 15-deoxy, Δ12,14 prostamide J2" Oncotarget, 11(52):4788-4802 (2020).

(Continued)

*Primary Examiner* — Brian J Davis
(74) *Attorney, Agent, or Firm* — Myers Bigel, P.A.

(57) ABSTRACT

Provided is a method of activating immune cells and/or an immune system response in a subject. The method may comprise administering to a subject an effective amount of a compound of Formula (I): or a prodrug, derivative, and/or salt thereof. In some embodiments, the method comprises contacting an immune cell with a compound of Formula (I) or a prodrug, derivative, and/or salt thereof. Also provided are compounds, compositions, and kits for activating immune cells and/or an immune system response in a subject.

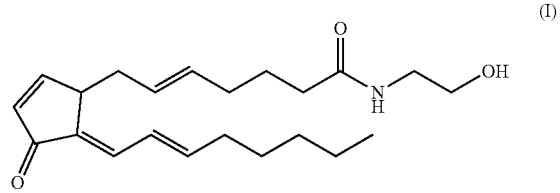

(I)

20 Claims, 10 Drawing Sheets

(56) References Cited

U.S. PATENT DOCUMENTS

| | | | |
|---|---|---|---|
| 5,900,252 | A | 5/1999 | Calanchi et al. |
| 5,948,433 | A | 9/1999 | Burton et al. |
| 5,952,366 | A | 9/1999 | Pandey et al. |
| 5,972,366 | A | 10/1999 | Haynes et al. |
| 5,983,134 | A | 11/1999 | Ostrow |
| 5,985,307 | A | 11/1999 | Hanson et al. |
| 5,985,317 | A | 11/1999 | Venkateshwaran et al. |
| 6,004,534 | A | 12/1999 | Langer et al. |
| 6,010,715 | A | 1/2000 | Wick et al. |
| 6,024,975 | A | 2/2000 | D et al. |
| 6,039,975 | A | 3/2000 | Shah et al. |
| 6,048,736 | A | 4/2000 | Kosak |
| 6,060,082 | A | 5/2000 | Chen et al. |
| 6,071,495 | A | 6/2000 | Unger et al. |
| 6,120,751 | A | 9/2000 | Unger |
| 6,131,570 | A | 10/2000 | Schuster et al. |
| 6,139,865 | A | 10/2000 | Friend et al. |
| 6,167,301 | A | 12/2000 | Flower et al. |
| 6,253,872 | B1 | 7/2001 | Neumann |
| 6,256,533 | B1 | 7/2001 | Yuzhakov et al. |
| 6,261,595 | B1 | 7/2001 | Stanley et al. |
| 6,267,983 | B1 | 7/2001 | Fujii et al. |
| 6,271,359 | B1 | 8/2001 | Norris et al. |
| 6,274,552 | B1 | 8/2001 | Tamarkin et al. |
| 6,316,652 | B1 | 11/2001 | Steliou |
| 6,680,299 | B2 | 1/2004 | Or et al. |
| 9,328,060 | B2 | 5/2016 | Van Dross et al. |
| 10,960,013 | B2 * | 3/2021 | Van Dross ............... A61P 17/12 |
| 2004/0023954 | A1 | 2/2004 | Ling et al. |
| 2012/0230968 | A1 | 9/2012 | Worden, Sr. |
| 2015/0111969 | A1 | 4/2015 | Van Dross et al. |

OTHER PUBLICATIONS

Obeid et al. "Calreticulin exposure dictates the immunogenicity of cancer cell death" Nature Medicine, 13(1):54-61 (2007).

International Search Report and the Written Opinion of the International Searching Authority corresponding to International Patent Application No. PCT/US2018/048806 (10 pages) (dated Oct. 16, 2018).

Dalod et al. "Dendritic cell maturation: functional specialization through signaling specificity and transcriptional programming" The EMBO Journal, 33(10):1104-1116 (2014).

Hangai et al. "PGE2 induced in and released by dying cells functions as an inhibitory DAMP" Proceedings of the National Academy of Sciences USA, 113(14):3844-3849 (2016).

Hernandez et al. "Damage-associated molecular patterns in cancer: a double-edged sword" Oncogene, 35:5931-41 (2016).

International Preliminary Report on Patentability corresponding to International Patent Application No. PCT/US2018/048806 (7 pages) (dated Mar. 3, 2020).

Krysko et al. "Immunogenic cell death and DAMPs in cancer therapy" Nature Reviews Cancer, 12:860-875 (2012).

Ladin et al. "Preclinical and Clinical Assessment of Cannabinoids as Anti-cancer Agents" Frontiers in Pharmacology, 7:361 (2016).

Lee et al. "Dengue virus-induced ER stress is required for autophagy activation, viral replication, and pathogenesis both in vitro and in vivo" Scientific Reports, 8(489):1-14 (2018).

Polin, R. A. "Monoclonal Antibodies Against Microorganisms" European Journal of Clinical Microbiology & Infectious Diseases, 3(5):387-398 (1984).

Rakestraw et al. "Antibody-targeted photolysis: in vitro studies with Sn(IV) chlorin e6 covalently bound to monoclonal antibodies using a modified dextran carrier" Proceedings of the National Academy of Sciences USA, 87(11):4217-4221 (1990).

Soliman et al. "Anandamide-Induced Endoplasmic Reticulum Stress and Apoptosis are mediated by Oxidative Stress in non-Melanoma Skin Cancer: Receptor-Independent Endocannabinoid Signaling" Molecular Carcinogenesis, 55(11):1807 (2016).

Soliman et al. "Arachidonoyl-ethanolamide Activates Endoplasmic Reticulum Stress-Apoptosis in Tumorigenic Keratinocytes: Role of Cyclooxygenase-2 and Novel J-series Prostamides" Molecular Carcinogenesis, 55(2):117-130 (2016).

Soliman et al. "Cannabinoids as Therapeutics for non-melanoma skin cancer" Journal of Dermatology and Clinical Research, 4(2):1069 (2016).

Su et al. "Japanese Encephalitis Virus Infection Initiates Endoplasmic Reticulum Stress and an Unfolded Protein Response" Journal of Virology, 76(9):4162-4171 (2002).

Zhang et al. "Virus-induced ER stress and the unfolded protein response" Frontiers in Plant Science, 3(293):1-16 (2012).

* cited by examiner

COMPOUNDS, COMPOSITIONS, KITS, AND METHODS FOR ACTIVATING IMMUNE CELLS AND/OR AN IMMUNE SYSTEM RESPONSE

RELATED APPLICATION INFORMATION

This application claims the benefit of U.S. Provisional Application Ser. No. 62/553,510, filed Sep. 1, 2017, the entire contents of which are incorporated by reference herein.

FIELD OF THE INVENTION

The present invention relates to compounds, compositions, kits and methods for activating immune cells and/or an immune system response in a subject using a J-series prostaglandin-ethanolamide, prodrug, derivative, and/or salt thereof.

BACKGROUND OF THE INVENTION

15deoxy, Δ12,14 Prostaglandin J2 (15dPGJ2-EA; see U.S. Pat. No. 9,328,060) is a novel molecule that has shown cytotoxic activity across several cancer types. It has been determined that 15dPGJ2-EA preferentially causes cell death in tumor cells compared to non-tumor cells and that this preference is initiated through induction of endoplasmic reticulum (ER) stress.

The endoplasmic reticulum (ER) is an organelle that is primarily responsible for folding proteins. ER stress occurs when the demand for protein folding exceeds the cells capacity to fold proteins leading to an accumulation in unfolded or misfolded proteins. In response to the accumulation of malformed proteins the cell attempts to relieve the stress or initiates death if the total cellular stress is insurmountable.

SUMMARY OF THE INVENTION

A first aspect of the present invention is directed to a method of activating immune cells and/or an immune system response in a subject, the method comprising administering to the subject an effective amount of a compound of Formula (I):

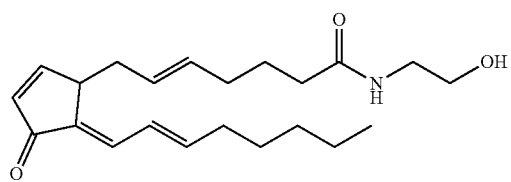

(I)

or a prodrug, derivative, and/or salt thereof.

Another aspect of the present invention is directed to a method of activating an immune cell, the method comprising contacting an immune cell (e.g., a T-cell and/or dendritic cell) with a compound of Formula (I) or a prodrug, derivative, and/or salt thereof to provide an engineered immune cell.

A further aspect of the present invention is directed to a composition comprising a compound of Formula (I) or a prodrug, derivative, and/or salt thereof.

Another aspect of the present invention is directed to a kit comprising a first container comprising a first pharmaceutical composition, wherein the first pharmaceutical composition comprises a first pharmaceutical carrier and a compound of Formula (I) or a prodrug, derivative, and/or salt thereof.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

DETAILED DESCRIPTION

Figure 1:
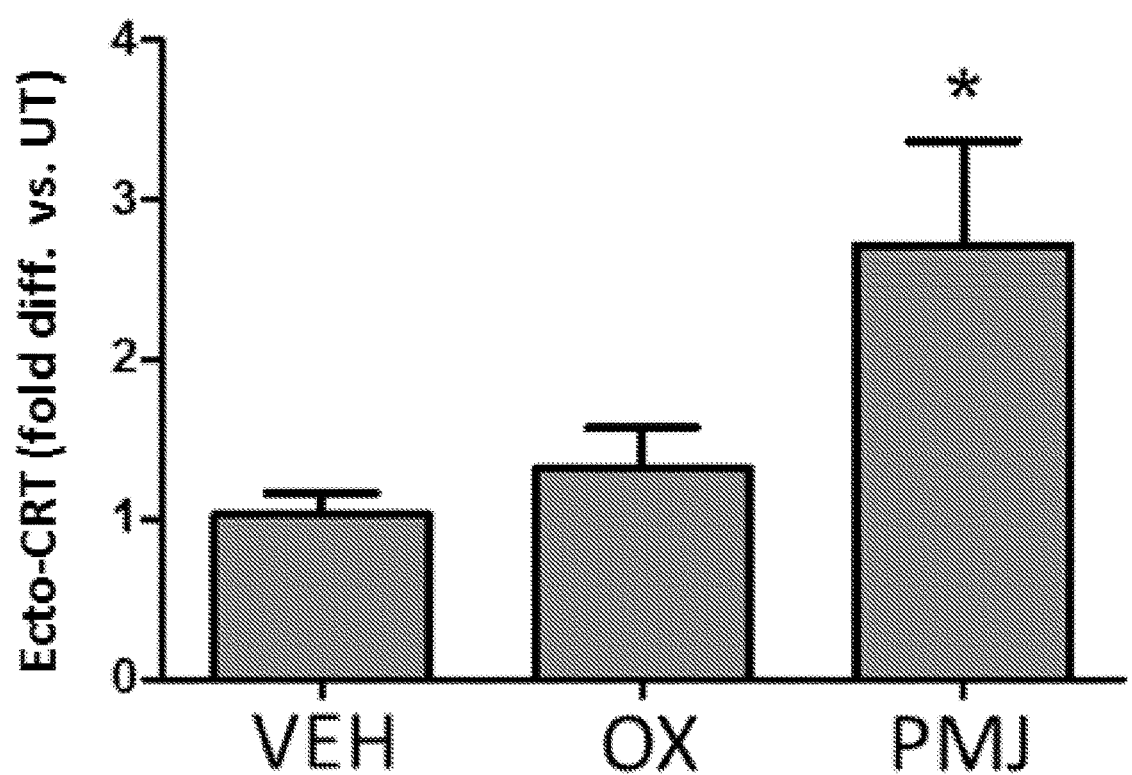
FIG. 1 is a graph showing the mean fluorescence (percentage from untreated) for cell surface calreticulin expression after exposure to (from left to right): vehicle, oxaliplatin, and 5 μM 15d-PMJ2.

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value such as an amount or concentration and the like, is meant to encompass variations of +10%, ±5%, ±1%, ±0.5%, or even ±0.1% of the specified value as well as the specified value. For example, "about X" where X is the measurable value, is meant to include X as well as variations off 10%, +5%, ±1%, ±0.5%, or even ±0.1% of X. A range provided herein for a measureable value may include any other range and/or individual value therein.

It will be understood that although the terms "first," "second," "third," "a)," "b)," and "c)," etc. may be used herein to describe various elements of the invention should not be limited by these terms. These terms are only used to distinguish one element of the invention from another. Thus, a first element discussed below could be termed a element aspect, and similarly, a third without departing from the teachings of the present invention. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims or figures unless specifically indicated otherwise.

As used herein, "one or more" can mean one, two, three, four, five, six, seven, eight, nine, ten or more, up to any number.

As used herein, the terms "increase," "increases," "increased," "increasing," "improve," "enhance," and similar terms indicate an elevation in the specified parameter of at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more.

As used herein, the terms "reduce," "reduces," "reduced," "reduction," "inhibit," and similar terms refer to a decrease in the specified parameter of at least about 5%, 10%, 15%, 20%, 25%, 30%, 35%, 40%, 45%, 50%, 55%, 60%, 65%, 70%, 75%, 80%, 85%, 90%, 95%, 97%, or 100%.

The terms "administering", "administered", "delivering", and grammatical variants thereof as used herein are meant to include topical, parenteral and/or oral administration, all of which are described herein. Parenteral administration includes, without limitation, intravenous, intraperitoneal, subcutaneous and/or intramuscular administration (e.g., skeletal muscle or cardiac muscle administration). In the methods of this invention, a compound or composition of this invention may be administered alone and/or simultaneously with one or more other compounds. In some embodiments, the compounds may be administered sequentially, in any order and at any time. It will be appreciated that the actual method, order, and/or time of administration may vary according to, inter alia, the particular preparation of compound(s) being utilized, and the particular formulation(s) of the one or more other compounds being utilized. The optimal method, order, and/or time of administration of the compounds of the invention for a given set of conditions can be ascertained by those skilled in the art using conventional techniques and in view of the information set out herein.

The terms "administering", "administered", "delivering", and grammatical variants thereof also refer, without limitation, to oral, sublingual, buccal, transnasal, transdermal, topical, rectal, intraperitoneal, intramuscular, intravenous, intraarterial (intracoronary), intraventricular, intrathecal, and subcutaneous routes. In accordance with good clinical practice, the instant compounds can be administered at a dose that will produce effective beneficial effects without causing undue harmful or untoward side effects, i.e., the benefits associated with administration outweigh the detrimental effects.

"Treat," "treating" or "treatment of" (and grammatical variations thereof) as used herein refer to any type of treatment that imparts a benefit to a subject and may mean that the severity of the subject's condition, disorder, disease, and/or illness is reduced, at least partially improved, or ameliorated and/or that some alleviation, mitigation or decrease in at least one clinical symptom associated with a condition, disorder, disease and/or illness is achieved and/or there is a delay in the progression of the symptom. In some embodiments, the severity of a symptom associated with cancer and/or tumor size may be reduced in a subject compared to the severity of the symptom and/or tumor size in the absence of a method of the present invention and/or compared to a conventional treatment.

In some embodiments, a compound of Formula (I) or the prodrug, derivative, and/or salt thereof and/or a composition of the present invention may be administered in a treatment effective amount. A "treatment effective" amount as used herein is an amount that is sufficient to treat (as defined herein) a subject. Those skilled in the art will appreciate that the therapeutic effects need not be complete or curative, as long as some benefit is provided to the subject. In some embodiments, a treatment effective amount may be achieved by administering a composition of the present invention.

The terms "prevent," "preventing" and "prevention" (and grammatical variations thereof) refer to avoidance, reduction and/or delay of the onset of a symptom associated with a condition, disorder, disease and/or illness (e.g., cancer and/or a tumor) and/or a reduction in the severity of the condition, disorder, disease and/or illness relative to what would occur in the absence of a method of the present invention and/or compared to a conventional treatment. The prevention can be complete, e.g., the total absence of the symptom. The prevention can also be partial, such that the occurrence of the symptom in the subject and/or the severity of onset is less than what would occur in the absence of a method of the present invention and/or compared to a conventional treatment.

In some embodiments, a compound of Formula (I) or the prodrug, derivative, and/or salt thereof and/or a composition of the present invention may be administered in a prevention effective amount. A "prevention effective" amount as used herein is an amount that is sufficient to prevent (as defined herein) a symptom associated with a condition, disorder, disease and/or illness (e.g., cancer and/or a tumor) in a subject. Those skilled in the art will appreciate that the level of prevention need not be complete, as long as some benefit is provided to the subject. In some embodiments, a prevention effective amount may be achieved by administering a composition of the present invention.

As appropriate, a treatment effective amount or a prevention effective amount in any individual case can be determined by one of ordinary skill in the art by reference to the pertinent texts and literature and/or by using routine experimentation. (See, for example, Remington, *The Science and Practice of Pharmacy* (latest edition)).

"15-deoxy $\Delta^{12,14}$PGJ$_2$-EA," "15dD12,14-PGJ$_2$-EA," "15d-PGJ$_2$-EA," 15-deoxy $\Delta^{12,14}$PMJ$_2$," 15dD12,14-PMJ$_2$" and "15d-PMJ$_2$-EA" refer to 15-deoxy $\Delta^{12,14}$-prostagladin J$_2$-ethanolamide having a structure as set forth in Formula (I):

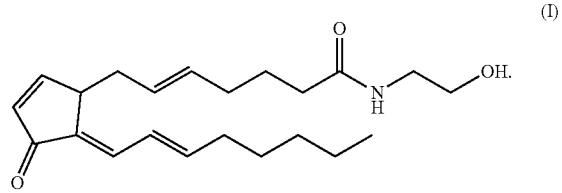 [SMILES: CCCCC/C=C/C=C1/C(=O)C=CC1C/C=C/CCCC(=O)NCCO]

"Prodrug" refers to a compound that is transformed in vivo and/or in vitro (e.g., in cultured cells and/or blood), such as, e.g., by hydrolysis in blood, to yield a pharmaceutically active drug. An example pharmaceutically active drug is the compound of Formula (I) or the ionic form and/or salt thereof. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299, which is incorporated herein by reference. Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound.

Particular prodrugs of the present invention include Prostaglandin D$_2$ ethanolamide (PGD$_2$-EA") as set forth in Formula (II):

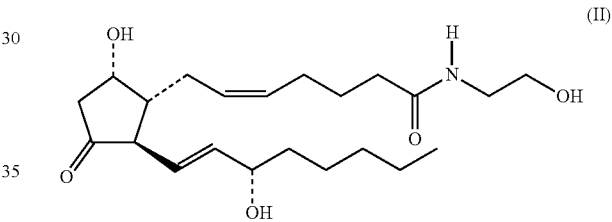

"Pharmaceutically acceptable" as used herein means that the compound, anion, or composition is suitable for administration to a subject to achieve the treatments described herein, without unduly deleterious side effects in light of the severity of the disease and necessity of the treatment.

"Salt" or "pharmaceutically acceptable salt" as used herein refers to a salt that retains the biological effectiveness of the free acids and bases of a specified compound and is not biologically or otherwise undesirable. Examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propionates, oxalates, malonates, succinates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates, propanesulfonates, naphthalene- 1 -sulfonates, naphthalene-2-sulfonates, and mandelates. In some embodiments, the salt is a hydrochloride, sulfite, benzoate, salicykate, cocoate, tallowate, undecylenate or carboxylate salt.

"Tissue-specific antigen" as used herein refers to an antigen that is characteristic of a tissue type, including specific tumor tissues. An example of a tissue-specific antigen expressed by a tumor tissue is the antigen prostatic acid phosphatase, which is present in over 90% of all prostate tumors.

"Antigen presenting cells" or "APC", as used herein refer to cells that are capable of activating T-cells, and include, but are not limited to, certain macrophages, B cells and dendritic cells.

"Dendritic cell" as used herein refers to any member of a diverse population of morphologically similar cell types found in lymphoid or non-lymphoid tissues. These cells are characterized by their distinctive morphology, high levels of surface MHC-class II expression (Steinman, et al., Ann. Rev. Immunol. 9:271 (1991); incorporated herein by reference for its description of such cells). These cells can be isolated from a number of tissue sources and from peripheral blood.

As used herein, the terms "mature(s)", "maturation" (e.g., dendritic cell maturation), and grammatical variations thereof refer to a functional reprogramming of an immune cell (e.g., a dendritic cell), characterized by the acquisition and/or increased ability of multiple properties. These properties include, but are not limited to, phagocytosis, antigen processing and presentation, migration, and T cell co-stimulation, as reviewed in Dalod et al. EMBO J. 33:1104-1116 (2014), incorporated herein by reference for its description of dendritic cell maturation.

The terms "phagocytosis," "phagocytose" and/or "phagocytic" as used herein refer to the process of antigen uptake by cells capable of performing this function (i.e., "phagocytic cells"), including, among others, dendritic cells and macrophages. Phagocytosis is a specialized method of uptake (i.e., "endocytosis") and internalization of extracellular antigen by phagocytic cells (e.g., dendritic cells or macrophages), wherein the antigen can be processed and presented upon the cellular surface of phagocytic cells to interact with (e.g., contact) and/or activate (e.g., reactivate) other immune cells such as, but not limited to, T cells and B cells. Phagocytic cells that are specialized for phagocytosis (e.g. "prophagocytic"), antigen processing and presentation, migration, and T cell co-stimulation may also be referred to interchangeably as "antigen presenting cells" ("APCs"), optionally as "professional APCs." The intracellular, cell surface, and/or extracellular processes and/or signals promoting phagocytosis of a target cell (e.g., a cancer and/or tumor cell) by a phagocytic cell are referred to herein as "phagocytic signaling" (e.g., pro-phagocytic signaling).

Provided herein are compounds, compositions, kits, and methods for activating immune cells and/or an immune system response in a subject. In some embodiments, a method of the present invention comprises administering to a subject an effective amount of a compound of Formula (I) or a prodrug, derivative, and/or salt thereof. In some embodiments, a compound of Formula (II) is administered to the subject.

In some embodiments, a method of the present invention comprises activating an immune cell, the method comprising contacting an immune cell (e.g., a T-cell and/or dendritic cell) with a compound of Formula (I) or a prodrug, derivative, and/or salt thereof to provide an engineered immune cell. "Contacting" and grammatical variations thereof, as used herein are intended to include mixing, adding, dissolving, combining, soaking, suspending, immersing, saturating, dipping, incorporating, wetting, submerging, spraying, administering and/or any variation and/or combination thereof. In some embodiments, the contacting step may comprise culturing the immune cell in media comprising the compound of Formula (I) or the prodrug, derivative, and/or salt thereof. In some embodiments, the contacting step may comprise administering the compound of Formula (I) or the prodrug, derivative, and/or salt thereof to a subject in a manner so that the compound of Formula (I) or the prodrug, derivative, and/or salt thereof is put in contact with the immune cell.

The immune cell may be contacted ex vivo and/or in vivo with the compound of Formula (I) or the prodrug, derivative, and/or salt thereof. The method may comprise culturing the engineered immune cell, optionally to provide a plurality of engineered immune cells. The immune cell may be any suitable immune cell and may be obtained from a donor. In some embodiments, the donor is a subject to be treated and/or administered the engineered immune cell and/or plurality of engineered immune cells (e.g., a patient), which may provide a personalized treatment. When the donor is not a subject to be treated and/or administered the engineered immune cell and/or plurality of engineered immune cells, the donor may be the same species as the subject and/or patient to be treated. In some embodiments, the immune cell is obtained from a subject and/or donor via apheresis.

When an immune cell is contacted ex vivo with the compound of Formula (I) or the prodrug, derivative, and/or salt thereof, the engineered immune cell and/or the plurality of engineered immune cells may be delivered to a subject. In some embodiments, the engineered immune cell and/or the plurality of engineered immune cells may be delivered to the subject via infusion.

In some embodiments, a method of the present invention comprises contacting an immune cell ex vivo with a compound of Formula (I) or a prodrug, derivative, and/or salt thereof to provide an engineered immune cell; delivering the engineered immune cell and/or a plurality of engineered immune cells to a subject; and/or administering to the subject the compound of Formula (I) or the prodrug, derivative, and/or salt thereof. The administering step may be carried out before, during, and/or after the contacting and/or delivering step.

A method of the present invention may administer the compound of Formula (I) or the prodrug, derivative, and/or salt thereof in an amount effective to activate host cell immunity in the subject. Host cell immunity in the subject may be activated against cancer cells and/or tumor cells, but may not be activated against non-cancer cells and/or non-tumor cells.

The cancer cells and/or tumor cells may be any suitable cancer cells and/or tumor cells such as, but not limited to, intestinal (small intestine, large intestine, colon), lung, breast, prostate, skin, bone, brain, liver, pancreatic, uterine, cervical, testicular, and/or ovarian cancer cells and/or tumor cells. In some embodiments, the cancer cells and/or tumor cells are skin cells and/or intestinal (e.g., colon) cells. In some embodiments, the cancer cells and/or tumor cells are drug resistant cells, metastatic tumor cells, and/or tumor stem stems.

In some embodiments, the compound of Formula (I) or the prodrug, derivative, and/or salt thereof may be administered in an amount effective to activate Damage Associated Molecular Pattern (DAMP)-immunogenic cell death (ICD) in the subject.

In some embodiments, a method of the present invention may reprogram and/or activate an immune cell (e.g., a dendritic cell) to attack and/or kill cancer cells and/or tumor cells, optionally in a subject. In some embodiments, a method of the present invention may activate antigen presenting cells (e.g., dendritic cells), optionally in a subject. In some embodiments, a method of the present invention activates (e.g., reactivates) and/or reprograms (e.g., matures) a dendritic cell to uptake, process, and/or present pathogen-derived or host-derived antigenic peptides to naïve T-cells in peripheral tissues, optionally in peripheral tissues in a subject. In some embodiments, a method of the present invention may induce an immune response against a tumor-associated antigen, optionally in a subject. In some embodiments, a method of the present invention may activate T-cells, optionally to produce a multivalent cellular immune response against a given antigen and the response may be greater than the response achieved with the given antigen alone. In some embodiments, a method of the present invention may induce maturation of an immune cell (e.g., a dendritic cell).

In some embodiments, when a cancer cell and/or tumor cell is exposed to (e.g., contacted and/or administered) a compound of Formula (I) or a prodrug, derivative, and/or salt thereof, DAMP expression occurs, which can include cell surface calreticulin expression, the release of ATP, and/or the release of HMGB1. DAMPs (e.g., ATP, HMGB1, and/or calreticulin) may bind to receptors on the surface of dendritic cells (DCs), which may cause DCs to express MHCII, CD80 and/or CD86 on its surface. The expression of MHCII, CD89, and/or CD86 on the surface of DCs is an indicator of the cell's maturity. In some embodiments, a method of the present invention may increase the expression of MHCII, CD89, and/or CD86 by at least about 5%, 10%, 15%, 20%, 25%, 30%, 35%, 40%, 45%, 50%, 55%, 60%, 65%, 70%, 75%, 80%, 85%, 90%, 95%, 100%, or more compared to the expression of MHCII, CD89, and/or CD86 in the absence of a method of the present invention and/or compared to a control. In some embodiments, mature DCs may phagocytose cancer and/or tumor cells and/or expose parts of the cancer and/or tumor cell to cytotoxic T cells (CD8+ T cells, CD4+ cells, and/or NK cells). In some embodiments, the cytotoxic T cells may attack the cancer and/or tumor cells. In some embodiments, a method of the present invention increases the number of immune cells (e.g., dendritic cells) that infiltrate and/or are present in a tumor by at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, or more compared to a control and/or compared to the number of infiltrating immune cells in the absence of a method of the present invention.

In some embodiments, a method of the present invention may increase phagocytic (e.g., pro-phagocytic) signaling in a subject, optionally wherein the increase in phagocytic (e.g, pro-phagocytic) signaling is in cancer and/or tumor cells in the subject. The increase in phagocytic signaling may be preferentially in cancer and/or tumor cells in the subject compared to non-cancerous and/or non-tumor cells in the subject. In some embodiments, the increase in phagocytic signaling in cancer and/or tumor cells in a subject is at least 2-, 3-, 4-, 5-, 6-, 7-, 8-, 9-, or 10-fold greater than phagocytic signaling in non-cancerous and/or non-tumor cells in the subject. In some embodiments, administering a compound of the present invention to a subject increases phagocytic signaling in cancer and/or tumor cells in a subject by at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, or more compared to a control (e.g., a vehicle) and/or compared to phagocytic signaling in the cells in the absence of a method of the present invention.

A method of the present invention may cause and/or provide protective immunity in the subject, optionally protective immunity may be against cancer cells and/or tumor cells of the same origin (e.g., cancer and/or tumor cells that are the same origin as cancer and/or tumor cells exhibiting increased ER stress and/or cytotoxic ER stress). In some embodiments, the cancer and/or tumor cells are those remaining in the subject after surgery, radiation therapy, and/or chemotherapy. In some embodiments, a method of the present invention provides immunogenic cell death of cancer cells and/or tumor cells in the subject. A method of the present invention may not result in and/or provide autoimmune side effects in the subject (e.g., autoimmune side effects observed with chemotherapeutic checkpoint inhibitors).

In some embodiments, a method of the present invention is selectively toxic to cells having an increased level of ER stress compared to normal cells of the same type. A method of the present invention may administer a compound of Formula (I) or the prodrug, derivative, and/or salt thereof in an amount effective to provide cytotoxic ER stress in cancer cells and/or tumor cells in the subject. In some embodiments, the method does not provide cytotoxic ER stress in non-cancer cells and/or non-tumor cells in the subject.

A method of the present invention may induce cell death via an ER-stress dependent mechanism. In some embodiments, the method may induce cell death in cancer cells, tumor cells, and/or in cells exhibiting increased ER stress (e.g., cells exhibiting increased ER stress during their growth cycle) compared to normal, healthy cells of the same type.

Studies with 15d-PGJ2-EA and tumor cells determined that the selective death in tumor cells was mediated by the induction of endoplasmic reticulum (ER) stress. In some embodiments, a compound and/or composition of the present invention can induce ER stress in cells and can push cells with moderate or greater levels of ER stress beyond their death threshold. In contrast, normal cells may contain low endogenous ER stress, and an equivalent amount of the compound and/or composition will not result in cell death of the normal cells, thereby producing selective toxicity. Selectively targeting the diseased cells may decrease the risk of developing adverse effects. Compounds, compositions, and/or methods of the present invention may comprise those as described in U.S. Pat. No. 9,328,060 and/or PCT/US17/20315, the contents of each of which are incorporated herein by reference.

In some embodiments, a method of the present invention may cause cell death in cells (e.g., cancer and/or tumor cells) exhibiting increased ER stress. In some embodiments, the increased ER stress is during the growth cycle of cells (e.g., infected cells). Cells treated by a method of the present invention may exhibit a level of ER stress that is at least about 10% (e.g., about 20%, 30%, 40%, 50%, 60%, 70%, 80%, 90%, 100%, 125%, 150%, 200%, or more) greater than the level of ER stress in a normal, healthy cell of the same type. The level of ER stress may be determined by the level of ER stress protein expression in the cells.

The ER is an intracellular organelle that is primarily responsible for folding newly synthesized proteins. ER stress occurs when the protein-folding demand exceeds the protein-folding capacity thereby causing misfolded or unfolded proteins to accumulate. In response to ER stress, cells decrease global translation, increase synthesis of protein-folding enzymes, and degrade misfolded or unfolded proteins to resolve the ER stress and survive. However, when ER stress is too severe, the ER stress machinery becomes overloaded and apoptotic death is initiated.

In some embodiments, a method of the present invention may be cytotoxic to cancer cells, tumor cells, and/or cells having an increased level of ER stress compared to normal, healthy cells. The method may provide increased cytotoxicity to such cells compared to a different method for treating and/or preventing cancer and/or tumor growth, such as, for example, one that does not administer a compound and/or composition of the present invention. In some embodiments, the cytotoxicity may be increased by at least about 10%, 15%, 20%, 25%, 30%, 35%, 40%, 45%, 50%, 55%, 60%, 65%, 70%, 75%, 80%, 85%, 90%, 95%, 98%, 99%, 100%, 150%, or more compared to a different method for treating and/or preventing cancer and/or tumor growth. Cytotoxicity may be determined using methods known to those of skill in the art, such as, for example, a qualitative reading of hematoxylin & eosin (H&E) slides, a lactate dehydrogenase (LDH) assay and/or a [3-(4, 5-Dimethylthiazol-2-yl)-5-(3-carboxymethoxyphenyl)-2-(4-sulfophenyl)-2H-tetrazolium, inner salt (MTS) assay. For administration, either the compound or pharmaceutical composition is understood as being or comprising the active ingredient (e.g., compound of Formula (I) or the prodrug, derivative, and/or salt thereof) and capable of administration to a subject, and thus, in some instances, the terms are interchangeable. Non-limiting methods of administration include, but are not limited to, oral, parenteral (e.g., subcutaneous, intramuscular, intradermal, intraperitoneal, or intravenous), inhalation spray (nasal and oral), topical (i.e., both skin and mucosal surfaces, including airway surfaces), transdermal, rectal, nasal, sublingual, buccal, or implanted reservoir administration, etc. In one embodiment, a composition of the present invention is administered topically or transdermally. In some embodiments, a composition of the present invention is administered topically. In yet another embodiment, a composition of the present invention is administered intraperitoneally.

The pharmaceutical compositions of the present invention may be suitably formulated for administration by any means known in the art. Non-limiting examples of forms of administration include, but are not limited to oral, parenteral (e.g., subcutaneous, intravenous, intramuscular, intra-articular, intra-synovial, intrasternal, intrathecal, intrahepatic, intralesional and intracranial injection or infusion techniques), inhalation spray (nasal and oral), topical (i.e., both skin and mucosal surfaces, including airway surfaces), transdermal, rectal, nasal, sublingual, buccal, or implanted reservoir administration, etc. In one embodiment, a composition of the present invention is administered topically or transdermally. For topical administration, suitable forms include, but are not limited to, suitable transdermal delivery systems known in the art, such as patches, and for nasal delivery, suitable forms include, but are not limited to, aerosol and nebulized delivery systems known in the art.

In some embodiments, a pharmaceutical composition of the present invention may be in the form suitable for topical administration. Non-limiting examples include, but are not limited to, pharmaceutical compositions in the form of a topical solution, ointment, cream, emulsion, a gel, a dispersion, a suspension, a foam, an aerosol, a droplet, an injectable form and/or a coating in which the active component may be suspended or dissolved in one or more carriers. A topical composition may be applied to body surfaces of a subject, including skin, mucous membranes, scalp, hair and/or nails. Carriers for topical administration of the compounds of this invention include, but are not limited to, mineral oil, liquid petrolatum, white petrolatum, propylene glycol, polyoxyethylene, polyoxypropylene compound, emulsifying wax and/or water. Where the topical formulation is in the form of an ointment or cream, suitable carriers include, but are not limited to, mineral oil, sorbitan monostearate, polysorbate 60, cetyl esters wax, cetearyl alcohol, 2 octyldodecanol, benzyl alcohol and/or water.

Methods of formulating pharmaceutical compositions have been described in numerous publications such as Pharmaceutical Dosage Forms: Tablets. Second Edition. Revised and Expanded. Volumes 1-3, edited by Lieberman et al.; Pharmaceutical Dosage Forms: Parenteral Medications. Volumes 1-2, edited by Avis et al.; and Pharmaceutical Dosage Forms: Disperse Systems. Volumes 1-2, edited by Lieberman et al.; published by Marcel Dekker, Inc, the disclosure of each of which are herein incorporated by reference in their entireties and for all purposes.

The pharmaceutical compositions are generally formulated as sterile, substantially isotonic and in full compliance with all Good Manufacturing Practice (GMP) regulations of the U.S. Food and Drug Administration.

In some embodiments, a method of the present invention may prevent and/or reduce the appearance (including reappearance) and/or size of a tumor. A method of the present invention may reduce the appearance and/or size of a tumor by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the appearance and/or size of a tumor prior to administering of a compound and/or composition of the present invention. The appearance and/or size of the tumor may be evaluated visually, such as, but not limited to, by the subject and/or a physician and/or by using a method known to those of skill in the art.

In some embodiments, the subject may see a reduction in the size and/or appearance of a tumor within 1, 2, 3, 4, 5, 6, 7, 8, 9, 10, 11, 12, 13, or more day(s) and/or week(s). In some embodiments, the method may reduce the size and/or appearance of a tumor in the skin of the subject with 12 weeks or less, in some embodiments, within 8 weeks or less, and in further embodiments, within 4 weeks or less.

A method of the present invention may reduce the number of tumors by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the number of tumors prior to administering of a compound and/or composition of the present invention. The number of tumors may be evaluated visually, such as, but not limited to, by the subject and/or a physician. The number of tumors may be determined using methods known to those of skill in the art.

A method of the present invention may decrease the rate of recurrence of a tumor in a subject by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the rate of recurrence of the same type of tumor in the absence of administering of a compound and/or composition of the present invention. The rate of recurrence may be determined using methods known to those of skill in the art. For example, after a treatment and/or removal of a tumor, the number of tumors may be visually determined and/or using a method known to those of skill in the art after a given period of time to determine the rate of recurrence.

A method of the present invention may prevent and/or reduce the risk of cancer and/or a tumor in a subject. In some embodiments, a method of the present invention may prevent and/or reduce the risk of cancer and/or a tumor in a subject by at least about 5%, 10%, 15%, 20%, 25%, 30%, 35%, 40%, 45%, 50%, 55%, 60%, 65%, 70%, 75%, 80%, 85%, 90%, 95%, 97% or 100% compared to the risk of the cancer and/or tumor in the absence of administering of a compound and/or composition of the present invention. The risk may be determined using methods known to those of skill in the art.

In some embodiments, the subject may be administered a second therapeutic agent and/or therapy (such as, e.g., chemotherapy or radiotherapy) prior to, at the same time, or after receiving a compound and/or composition of the present invention. In some embodiments, the second therapeutic agent comprises chimeric antigen receptor (CAR) T cells. In some embodiments, the second therapeutic agent is a checkpoint inhibitor and/or chemotherapeutic agent (e.g., a cytotoxic chemotherapeutic agent). Example check point inhibitors include, but are not limited to, nivolumab (Bristol-Myers Squibb), pembrolizumab (KEYTRUDA®, Merck), pidilizumab (Curetech), AMP-224 (GlaxoSmithKline/Amplimmune), MPDL3280A (Roche), MDX-1 105 (Medarex, Inc./Bristol Myer Squibb), MEDI-4736 (Medimmune/AstraZeneca), arelumab (Merck Serono), tremelimumab (Pfizer), pidilizumab (CureTech, Ltd.), IMP321 (Immutep S.A.), MGA271 (Macrogenics), BMS-986016 (Bristol-Meyers Squibb), lirilumab (Bristol-Myers Squibb), urelumab (Bristol-Meyers Squibb), PF-05082566 (Pfizer), IPH2101 (Innate Pharma/Bristol-Myers Squibb), MEDI-6469 (MedImmune/AZ), CP-870,893 (Genentech), Mogamulizumab (Kyowa Hakko Kirin), Varlilumab (CellDex Therapeutics), Avelumab (EMD Serono), Galiximab (Biogen Idee), AMP-514 (Amplimmune/AZ), AUNP 12 (Aurigene and Pierre Fabre), Indoximod (NewLink Genetics), NLG-919 (NewLink Genetics), INCB024360 (Incyte) and/or ipilimumab (YERVOY, (Bristol-Myers Squibb). Further example check point inhibitors include, but are not limited to, an inhibitor of Programmed Death 1 (PD-1, CD279), an inhibitor of Programmed Death -Ligand 1 (PD-L1, also known as B7-H1 and CD274), an inhibitor of PD-L2 (B7-DC, CD273), and/or an inhibitor of CTLA-4. In some embodiments, a therapeutic agent (e.g., an immune check point inhibitor) may target a PD-1 receptor and/or a CTLA-4 antigen.

It should also be understood that a specific dosage and treatment regimen for any particular patient will depend upon a variety of factors, including but not limited to, the age, body weight, general health, gender, diet, time of administration, rate of excretion, drug combination, and/or the judgment of the treating physician and/or the severity of the particular disease being treated.

In some embodiments, a compound and/or composition of the present invention may be administered (e.g., topically administered) to a subject using any method known to those of skill in the art. In some embodiments, the compound and/or composition may be administered (e.g., topically applied) to the subject at least 1, 2, 3, or more times per day. In some embodiments, the compound and/or composition may be administered (e.g., topically applied) to the subject at least 1, 2, 3, 4, 5, 6, 7, 8, or more times per week and/or month. In some embodiments, the compound and/or composition may be administered to the subject once daily, twice daily, every other day, every third day, once per week, or twice per week. In some embodiments, the compound and/or composition may be administered at least once daily for an extended period of time (e.g., a week, month, 2 months, etc.) and/or until the cancer and/or tumor has been treated and/or prevented. In some embodiments, the compound and/or composition may be applied on an as needed basis.

The present invention finds use in both veterinary and medical applications. Subjects suitable to be treated with a method of the present invention include, but are not limited to, mammalian subjects. Mammals of the present invention include, but are not limited to, canines, felines, bovines, caprines, equines, ovines, porcines, rodents (e.g. rats and mice), lagomorphs, primates (e.g., simians and humans), non-human primates (e.g., monkeys, baboons, chimpanzees, gorillas), and the like, and mammals in utero. Any mammalian subject in need of being treated according to the present invention is suitable. Human subjects of both genders and at any stage of development (i.e., neonate, infant, juvenile, adolescent, adult) may be treated according to the present invention. In some embodiments of the present invention, the subject is a mammal and in certain embodiments the subject is a human. The human subjects may be male or female and may be of any race or ethnicity, including, but not limited to, Caucasian, African-American, African, Asian, Hispanic, Indian, etc. Human subjects include both males and females of all ages including fetal, neonatal, infant, juvenile, adolescent, adult, and geriatric subjects as well as pregnant subjects. In particular embodiments of the present invention, the subject is a human adolescent and/or adult.

A method of the present invention may also be carried out on animal subjects, particularly mammalian subjects such as mice, rats, dogs, cats, livestock and horses for veterinary purposes, and/or for drug screening and drug development purposes.

In some embodiments, the subject is "in need of" or "in need thereof" a method of the present invention, for example, the subject has findings typically associated with cancer and/or a tumor, is suspected to have cancer and/or a tumor, and/or the subject has cancer and/or a tumor. In some embodiments, a subject has cancer such as, e.g., melanoma, non-melanoma skin cancer, colon cancer, etc. In some embodiments, a subject has a viral infection such as, e.g., human papilloma virus (HPV) and/or herpesvirus, and/or has findings typically associated with a viral infection such as, e.g., warts and/or cancer.

The compounds of the present invention may be formulated as the sole pharmaceutically active ingredient in a composition of the present invention or may be combined with other active ingredients.

A composition of the present invention may contain one or more compounds of the present invention. In some embodiments, the compounds may be formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel, Introduction to Pharmaceutical Dosage Forms, Fourth Edition 1985, 126).

In the compositions, effective concentrations of one or more compounds or pharmaceutically acceptable derivatives thereof may be (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions may be effective for delivery of an amount, upon administration, that treats, prevents, and/or ameliorates one or more of the symptoms of diseases or disorders associated with cancer and/or tumor.

In one embodiment, the compositions are formulated for single dosage administration. To formulate a composition, the weight fraction of a compound of the present invention is dissolved, suspended, dispersed or otherwise mixed in a selected carrier at an effective concentration such that the treated condition is relieved, prevented, or one or more symptoms may be ameliorated.

The active compound may be included in the pharmaceutically acceptable carrier in an amount sufficient to exert a therapeutically useful effect in the absence of undesirable side effects on the subject treated. The therapeutically effective concentration may be determined empirically by testing the compounds in in vitro and in vivo systems described herein and in U.S. Pat. No. 5,952,366 to Pandey et al. (1999) and then extrapolated therefrom for dosages for humans.

The concentration of active compound in the pharmaceutical composition may depend on absorption, inactivation and excretion rates of the active compound, the physicochemical characteristics of the compound, the dosage schedule, and/or the amount administered as well as other factors known to those of skill in the art. For example, the amount that is delivered may be sufficient to ameliorate one or more of the symptoms of cancer and/or a tumor as described herein.

In one embodiment, a therapeutically effective dosage should produce a serum concentration of the active ingredient of from about 0.1 ng/ml to about 50-100 ug/ml. In one embodiment, a therapeutically effective dosage is from 0.001, 0.01 or 0.1 to 10, 100 or 1000 mg of active compound per kilogram of body weight per day. Pharmaceutical dosage unit forms may be prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN™, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion, gel, or the like. The form of the resulting mixture depends upon a number of factors, including the intended mode of administration and the solubility of the compound in the selected carrier or vehicle. The effective concentration may be sufficient for ameliorating the symptoms of the disease, disorder or condition treated and may be empirically determined.

The pharmaceutical compositions may be provided for administration to humans and/or animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions may, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient by weight of the composition, in one embodiment 0.1-95% by weight of the composition, in another embodiment 75-85% by weight of the composition, and in another embodiment 0.5%-50% by weight of the composition.

In some embodiments, a composition of the present invention may be suitable for oral administration. Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, in one embodiment, capsules or tablets. The tablets, pills, capsules, troches and the like may contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, gellan gum, sodium carboxymethylcellulose, polyethylene glycol 4000 and cellulose acetate phthalate.

The compound, or pharmaceutically acceptable derivative thereof, may be provided in a composition that protects it from the acidic environment of the stomach. For example, the composition may be formulated in an enteric coating that maintains its integrity in the stomach and releases the active compound in the intestine. The composition may also be formulated in combination with an antacid or other such ingredient. When the dosage unit form is a capsule, it may contain, in addition to material of the above type, a liquid carrier such as a fatty oil. In addition, dosage unit forms may contain various other materials which modify the physical form of the dosage unit, for example, coatings of sugar and other enteric agents. The compounds may be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials may also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative.

An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms. Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, xanthan gum, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation. For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations may include those set forth in U.S. Pat. Nos. RE28,819 and 4,358,603. Briefly, such formulations may include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and/or one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and/or its esters, and/or dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and/or ethanol. Acetals include, but are not limited to, di(loweralkyl) acetals of loweralkyl aldehydes such as acetaldehyde diethyl acetal.

Parenteral administration, in one embodiment characterized by injection, either subcutaneously, intramuscularly or intravenously is also contemplated herein. Injectables may be prepared in conventional forms, either as liquid solutions or suspensions, solid forms suitable for solution or suspension in liquid prior to injection, or as emulsions. The injectables, solutions and emulsions may also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein may be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and/or ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and/or polypropylene glycol and/or mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and/or other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and/or peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and/or benzethonium chloride. Isotonic agents include sodium chloride and dextrose. Buffers include phosphate and/or citrate. Antioxidants include sodium bisulfate. Local anesthetics include procaine hydrochloride. Suspending and dispersing agents include sodium carboxymethylcelluose, xanthan gum, hydroxypropyl methylcellulose and/or polyvinylpyrrolidone. Emulsifying agents include Polysorbate 80 (TWEEN™ 80). A sequestering or chelating agent of metal ions includes EDTA. Pharmaceutical carriers may also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the subject or animal as is known in the art.

The unit-dose parenteral preparations may be packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized powders, which can be reconstituted for administration as solutions, emulsions and other mixtures, may also be used to carry out the present invention. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical mixtures may be prepared as described for the local and systemic administration. The resulting mixture may be a solution, suspension, emulsions or the like and may be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126; 4,414,209; and 4,364,923, which describe aerosols for delivery of a steroid useful for treatment of inflammatory diseases, particularly asthma). These formulations for administration to the respiratory tract may be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and/or mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients may be administered. These solutions, particularly those intended for ophthalmic use, may be formulated as 0.01% -10% isotonic solutions, pH about 5-7, with appropriate salts.

Other routes of administration, such as transdermal patches, including iontophoretic and electrophoretic devices, and/or rectal administration, are also contemplated herein.

Transdermal patches, including iontophoretic and electrophoretic devices, are well known to those of skill in the art. For example, such patches are disclosed in U.S. Pat. Nos. 6,267,983; 6,261,595; 6,256,533; 6,167,301; 6,024,975; 6,010715; 5,985,317; 5,983,134; 5,948,433 and 5,860,957.

For example, pharmaceutical dosage forms for rectal administration are rectal suppositories, capsules and tablets for systemic effect. Rectal suppositories as used herein mean solid bodies for insertion into the rectum which melt or soften at body temperature releasing one or more pharmacologically or therapeutically active ingredients. Pharmaceutically acceptable substances utilized in rectal suppositories are bases or vehicles and/or agents to raise the melting point. Examples of bases include cocoa butter (theobroma oil), glycerin-gelatin, carbowax (polyoxyethylene glycol) and appropriate mixtures of mono-, di- and/or triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, may be about 2 to 3 gm.

Tablets and capsules for rectal administration are manufactured using the same pharmaceutically acceptable substance and by the same methods as for formulations for oral administration.

The compounds provided herein, or pharmaceutically acceptable derivatives thereof, may also be formulated to be targeted to a particular tissue, receptor, infecting agent or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542 and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

In another embodiment, the disclosed compounds may be targeted to specific target tissues or target compositions using ligands specific for the target tissue or target composition, for example, using ligands or ligand-receptor pairs such as antibodies and antigens. Antibodies against tumor antigens and against pathogens are known. For example, antibodies and antibody fragments which specifically bind markers produced by or associated with tumors or infectious lesions, including viral, bacterial, fungal and parasitic infections, and antigens and products associated with such microorganisms have been disclosed, inter alia, in Hansen et al., U.S. Pat. No. 3,927,193 and Goldenberg, U.S. Pat. Nos. 4,331,647; 4,348,376; 4,361,544; 4,468,457; 4,444,744; 4,818,709 and 4,624,846. Antibodies against an antigen, e.g., a gastrointestinal, lung, breast, prostate, ovarian, testicular, brain or lymphatic tumor, a sarcoma or a melanoma, may be used.

A wide variety of monoclonal antibodies against infectious disease agents have been developed, and are summarized in a review by Polin, in Eur. J. Clin. Microbiol., 3(5): 387-398 (1984), showing ready availability. These include monoclonal antibodies (MAbs) against pathogens and their antigens such as the following: Anti-bacterial Mabs such as those against *Streptococcus agalactiae, Legionella pneumophilia, Streptococcus pyogenes, Escherichia coli, Neisseria* gonorrhosae, Neisseria meningitidis, Pneumococcus, Hemophilis influenzae B, Treponema pallidum, Lyme disease, spirochetes, Pseudomonas aeruginosa, Mycobacterium leprae, Brucella abortus, Mycobacterium tuberculosis, Tetanus toxin, Anti-protozoan Mabs such as those against Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Mesocestoides corti, Emeria tenella, Onchocerca volvulus, Leishmania tropica, Trichinella spiralis, Theileria parva, Taenia hydatigena, Taenia ovis, Taenia saginata, Anti-viral MAbs such as those against HIV-1, -2, and -3, Hepatitis A, B, C, D, Rabies virus, Influenza virus, Cytomegalovirus, Herpes simplex I and II, Human serum parvo-like virus, Respiratory syncytial virus, Varicella-Zoster virus, Hepatitis B virus, Measles virus, Adenovirus, Human T-cell leukemia viruses, Epstein-Barr virus, Mumps virus, Sindbis virus, Mouse mammary tumor virus, Feline leukemia virus, Lymphocytic choriomeningitis virus, Wart virus, Blue tongue virus, Sendai virus, Reo virus, Polio virus, Dengue virus, Rubella virus, Murine leukemia virus, Antimycoplasmal MAbs such as those against Acholeplasma laidlawii, Mycoplasma arthritidis, M hyorhinis, M orale, M arginini, M pneumonia; etc.

Suitable MAbs have been developed against most of the micro-organisms (bacteria, viruses, protozoa, other parasites) responsible for the majority of infections in humans, and many have been used previously for in vitro diagnostic purposes. These antibodies, and newer MAbs that can be generated by conventional methods, may be appropriate for use as target agents with the compounds provided herein.

It should be noted that mixtures of antibodies and immunoglobulin classes may be used, as may hybrid antibodies. Multispecific, including bispecific and hybrid, antibodies and antibody fragments may be used in the methods of the present invention for detecting and treating target tissue and may comprise at least two different substantially monospecific antibodies or antibody fragments, wherein at least two of the antibodies or antibody fragments specifically bind to at least two different antigens produced or associated with the targeted lesion or at least two different epitopes or molecules of a marker substance produced or associated with the target tissue. Multispecific antibodies and antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. Nos. 4,474,893 and 4,479,895, and in Milstein et al., Immunol. Today 5: 299 (1984).

Antibody fragments useful in the present invention include $F(ab')_2$, $F(ab)_2$, Fab', Fab, Fv and the like including hybrid fragments. In some embodiments, fragments are Fab', $F(ab')_2$, Fab, and $F(ab)_2$. Also useful are any subfragments retaining the hypervariable, antigen-binding region of an immunoglobulin and having a size similar to or smaller than a Fab' fragment. This will include genetically engineered and/or recombinant proteins, whether single-chain or multiple-chain, which incorporate an antigen-binding site and otherwise function in vivo as targeting vehicles in substantially the same way as natural immunoglobulin fragments. Such single-chain binding molecules are disclosed in U.S. Pat. No. 4,946,778, which is hereby incorporated by reference. Fab' antibody fragments may be conveniently made by reductive cleavage of $F(ab')_2$ fragments, which themselves may be made by pepsin digestion of intact immunoglobulin. Fab antibody fragments may be made by papain digestion of intact immunoglobulin, under reducing conditions, or by cleavage of $F(ab)_2$ fragments which result from careful papain digestion of whole immunoglobulin.

A ligand or one member of a ligand-receptor binding pair may be conjugated to the compounds provided herein for targeting the compounds to specific target tissues or target compositions. Examples of ligand-receptor binding pairs are set out in U.S. Pat. Nos. 4,374,925 and 3,817,837, the teachings of which are incorporated herein by reference.

Many compounds that can serve as targets for ligand-receptor binding pairs, and more specifically, antibodies, have been identified, and the techniques to construct conjugates of such ligands to compounds are well known to those of ordinary skill in this art. For example, Rakestraw et al. teaches conjugating Sn(IV) chlorine6 via covalent bonds to monoclonal antibodies using a modified dextran carrier (Rakestraw, S. L., Tompkins, R. D., and Yarmush, M. L., Proc. Nad. Acad. Sci. USA 87: 4217-4221 (1990). The compounds disclosed herein may also be conjugated to a ligand, such as an antibody, by using a coupling agent. Any bond which is capable of linking the components such that they are stable under physiological conditions for the time needed for administration and treatment is suitable. In some embodiments, the bond may be a covalent linkage. The link between two components may be direct, e.g., where a compound is linked directly to a targeting agent, or indirect, e.g., where a compound is linked to an intermediate and that intermediate being linked to the targeting agent.

A coupling agent should function under conditions of temperature, pH, salt, solvent system, and other reactants that substantially retain the chemical stability of the compound, the backbone (if present), and the targeting agent. Coupling agents should link component moieties stably, but such that there is only minimal or no denaturation or deactivation of the compound or the targeting agent. Many coupling agents react with an amine and a carboxylate, to form an amide, or an alcohol and a carboxylate to form an ester. Coupling agents are known in the art (see, e.g., M. Bodansky, "Principles of Peptide Synthesis", 2nd ed., and T. Greene and P. Wuts, "Protective Groups in Organic Synthesis," 2nd Ed, 1991, John Wiley, NY).

The compounds or pharmaceutically acceptable derivatives thereof may be packaged as articles of manufacture containing packaging material and a compound or pharmaceutically acceptable derivative thereof provided herein, which is effective for modulating the activity of cancer and/or a tumor, or for treatment, prevention or amelioration of one or more symptoms associated with cancer and/or a tumor or in which cancer and/or a tumor is implicated. The articles of manufacture may further comprise a label that indicates that the compound or composition, or pharmaceutically acceptable derivative thereof, is used for modulating the activity of cancer and/or a tumor, or for treatment, prevention or amelioration of one or more symptoms associated with a cancer and/or a tumor or in which cancer and/or a tumor is implicated.

The articles of manufacture provided herein contain packaging materials. Packaging materials for use in packaging pharmaceutical products are well known to those of skill in the art. See, e.g., U.S. Pat. Nos. 5,323,907; 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for cancer and/or a tumor.

Embodiments of the present invention also provide kits, which may include the elements necessary to carry out the therapies described above. In some embodiments, a kit may comprise a carrier being compartmentalized to receive in close confinement therein one or more containers, such as tubes or vials. One or more of the containers may contain a compound described herein. One or more containers may contain one or more enzymes or reagents to be utilized in desired reactions. These enzymes may be present by themselves or in admixtures, in lyophilized form or in appropriate buffers. The kit may contain all of the additional elements necessary to carry out the methods of the invention.

In some embodiments, a kit of the present invention comprises a first container comprising a pharmaceutical composition of the present invention. In some embodiments, the composition comprises a pharmaceutical carrier and a compound of Formula (I) or a prodrug or derivative thereof, and salts thereof.

In some embodiments, the kit may comprise a second pharmaceutical composition, wherein the second pharmaceutical composition comprises a second pharmaceutical carrier and a second therapeutic. The kit may separately store the first and second composition, optionally in separate containers. Any suitable additional therapeutic agent may be present in the second composition. In some embodiments, the second therapeutic is a checkpoint inhibitor and/or chemotherapeutic agent (e.g., a cytotoxic chemotherapeutic agent).

It is understood that the combinations of all embodiments described herein are also envisaged in the present invention.

The present invention will now be described in more detail with reference to the following examples. However, these examples are given for the purpose of illustration and are not to be construed as limiting the scope of the invention.

EXAMPLES

Example 1

DAMPs are proteins that are expressed on the surface of cancer cells (e.g., calreticulin (CRT)) or are released from cancer cells (e.g., ATP and HMGB1) after exposure to DAMP inducing agents. DAMPs signal immune cell mediated cancer death.

B16F10 melanoma cells were treated with 5 uM 15dPMJ2 (PMJ), 5 uM oxaliplatin (OX), drug vehicle (VEH, DMSO 0.1%) or cells remained untreated (UT) for 2 hours. After 2 hours, cell surface calreticulin (CRT) expression was measured by flow cytometric analysis. As shown in FIG. 1, 15dPMJ2-mediated cell surface CRT expression is significantly greater than oxaliplatin, which is a known DAMP inducer.

Example 2

Figure 2:
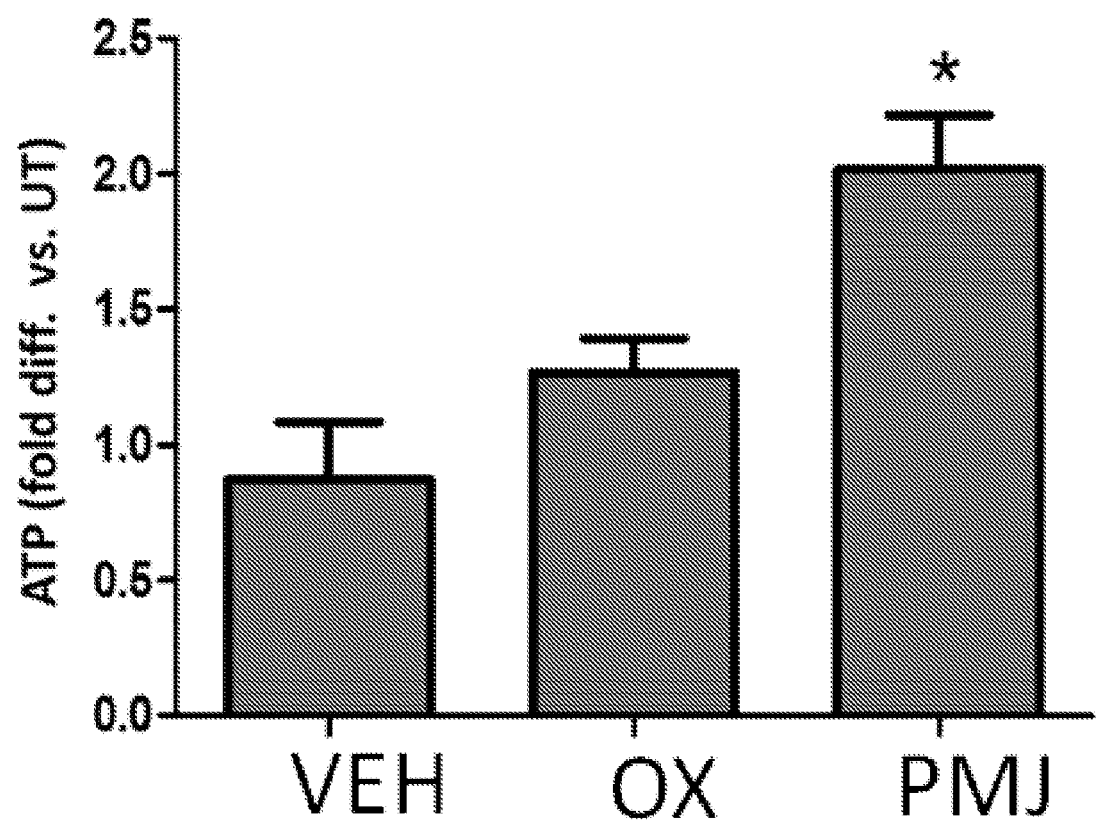
FIG. 2 is a graph of the amount of extracellular ATP released (compared to untreated) at 4 hours after exposure to (from left to right): vehicle, oxaliplatin, and 5 μM 15d-PMJ2.

B16F10 melanoma cells were treated with 5 uM 15dPMJ2 (PMJ), 5uM oxaliplatin (OX), drug vehicle (VEH, DMSO 0.1%) or cells remained untreated (UT) for 4 hours. After 4 hours of drug treatment, the cell culture media from B16F10 cells was obtained to measured ATP levels. As shown in FIG. 2, 15dPMJ2 significantly increased ATP release compared to vehicle and oxaliplatin treated cells.

Example 3

Figure 3:
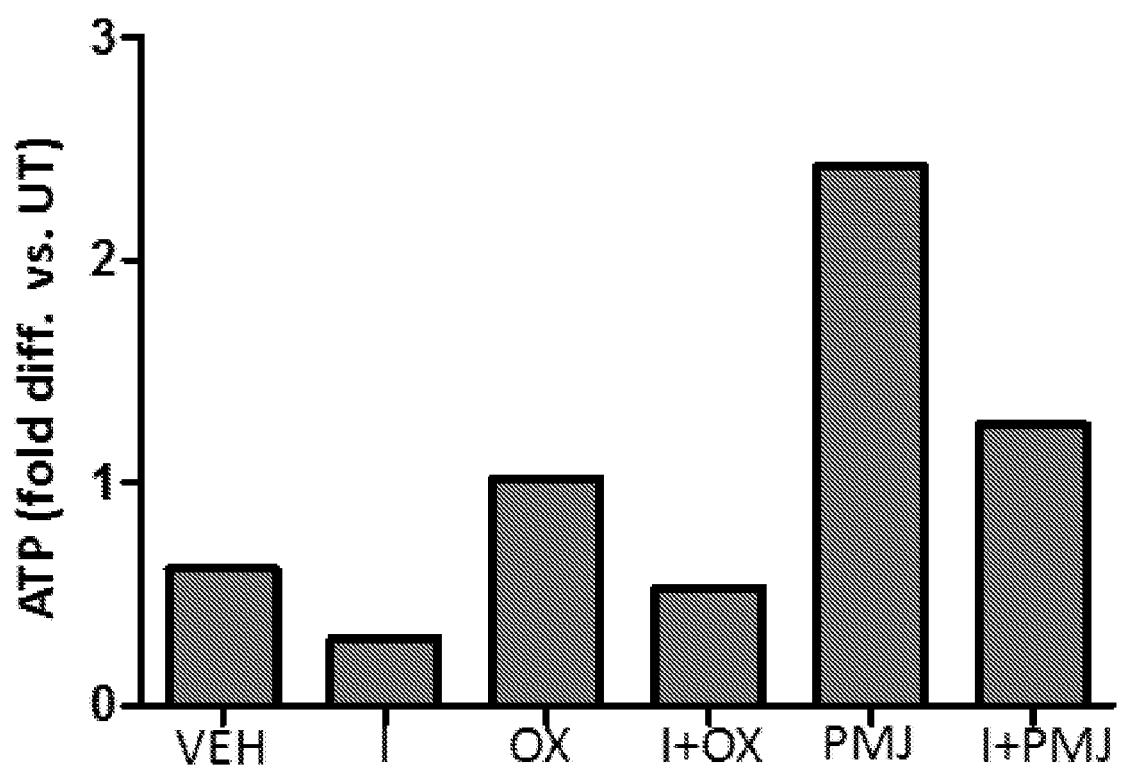
FIG. 3 is a graph of the amount of extracellular ATP released (compared to untreated) after exposure to (from left to right): vehicle, ER stress inhibitor (I) (GSK265615), oxaliplatin, inhibitor+oxaliplatin, 15dPMJ2, inhibitor+15dPMJ2.

B16F10 cells were treated with 15dPMJ2 (PMJ), oxaliplatin (OX), or drug vehicle (VEH) in the presence or absence of the ER stress inhibitor, GSK2656157 ("inhibitor" (I)). As shown in FIG. 3, the inhibitor significantly decreased extracellular ATP levels demonstrating that ER stress is required for 15dPMJ2-mediated ATP secretion.

Example 4

Brefeldin A is a molecule that inhibits the movement of proteins from the ER to the golgi apparatus (inhibits ER-golgi trafficking). Proteins must move from the ER to golgi in order translocate to the cell surface.

Figure 4:
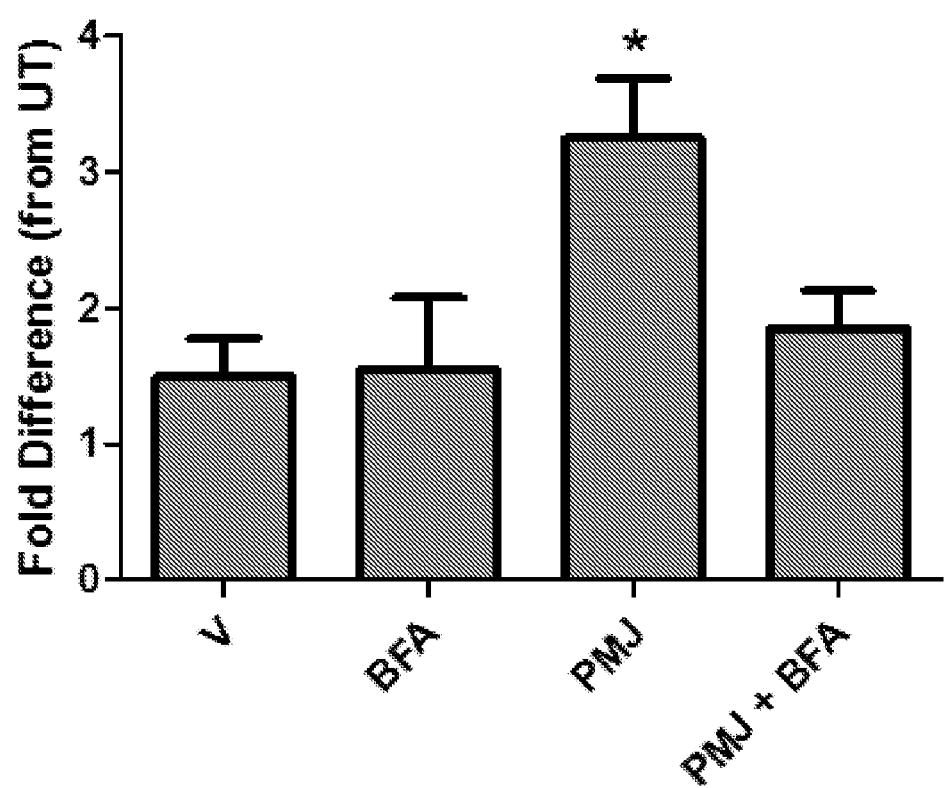
FIG. 4 is a graph showing the mean fluorescence (percentage from untreated) for cell surface calreticulin expression after exposure to (from left to right): vehicle, brefeldin A (BFA), 15d-PMJ2, and 15dPMJ2+BFA.

B16f10 cells were treated with vehicle (V), brefeldin A (BFA), 15dPMJ2 (PMJ) or brefeldin+15dPMJ2. As shown in FIG. 4, Brefeldin A inhibited 15dPMJ2-mediated cell surface CRT expression which demonstrates that the ER is essential for DAMP expression.

Example 5

15dPMJ2 also causes DAMP expression in non-melanoma skin cancer (NMSC) and colon cancer cells.

Figure 5:
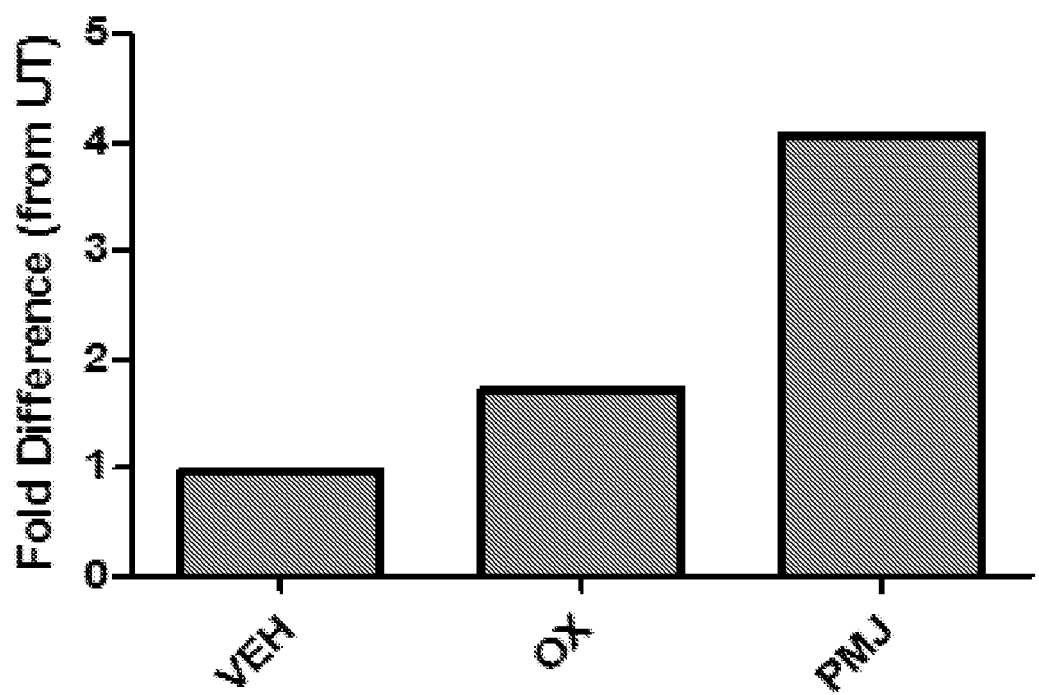
FIG. 5 is a graph showing the mean fluorescence (percentage from untreated) for cell surface calreticulin expression after exposure to (from left to right): vehicle, oxaliplatin, and 5 μ,M 15d-PMJ2 in non-melanoma skin cancer (NMSC) A431 cells.
Figure 6:
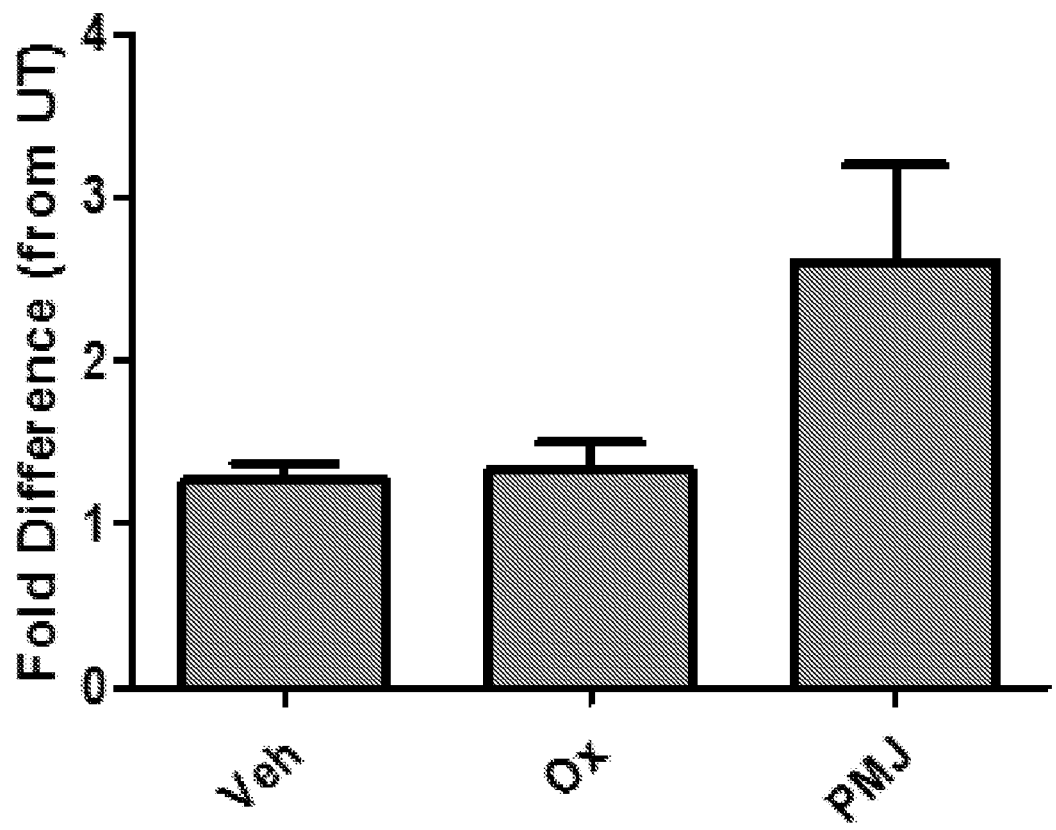
FIG. 6 is a graph showing the mean fluorescence (percentage from untreated) for cell surface calreticulin expression after exposure to (from left to right): vehicle, oxaliplatin, and 5 μM 15d-PMJ2 in colon cancer HT-29 cells.

A431 cells (NMSC) and HT-29 (colon cancer) cells were treated with 15dPMJ2, oxaliplatin (OX), drug vehicle (VEH) or cells were untreated (UT) for 2 hours. Cell surface CRT expression was then detected by flow cytometric analysis. As shown in FIGS. 5 and 6, 15dPMJ2 is a potent inducer of DAMP expression in different cancer cell types.

Example 6

15dPMJ2 preferentially increases pro-phagocytic signaling in NMSC.

Figure 7:
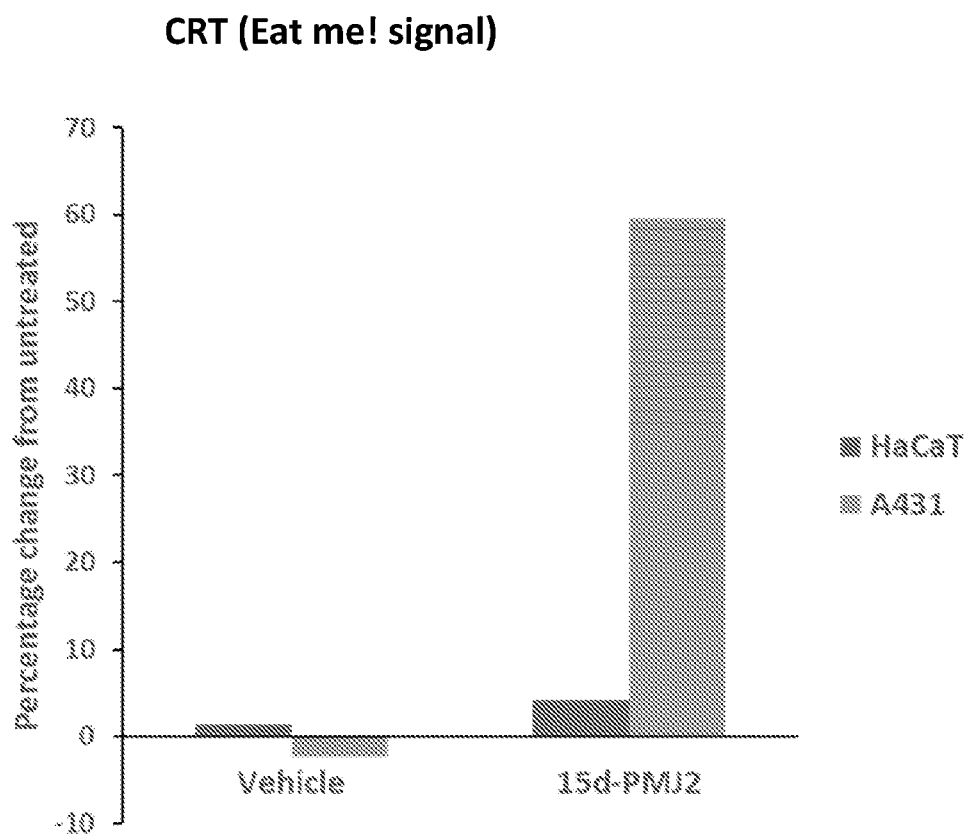
FIG. 7 is a graph showing the mean fluorescence (percentage change from untreated) for cell surface calreticulin expression after exposure to vehicle or 15d-PMJ2 in either (left) human non-tumorigenic keratinocyte HaCaT cells or (right) human non-melanoma skin cancer cells A431.
Figure 8:
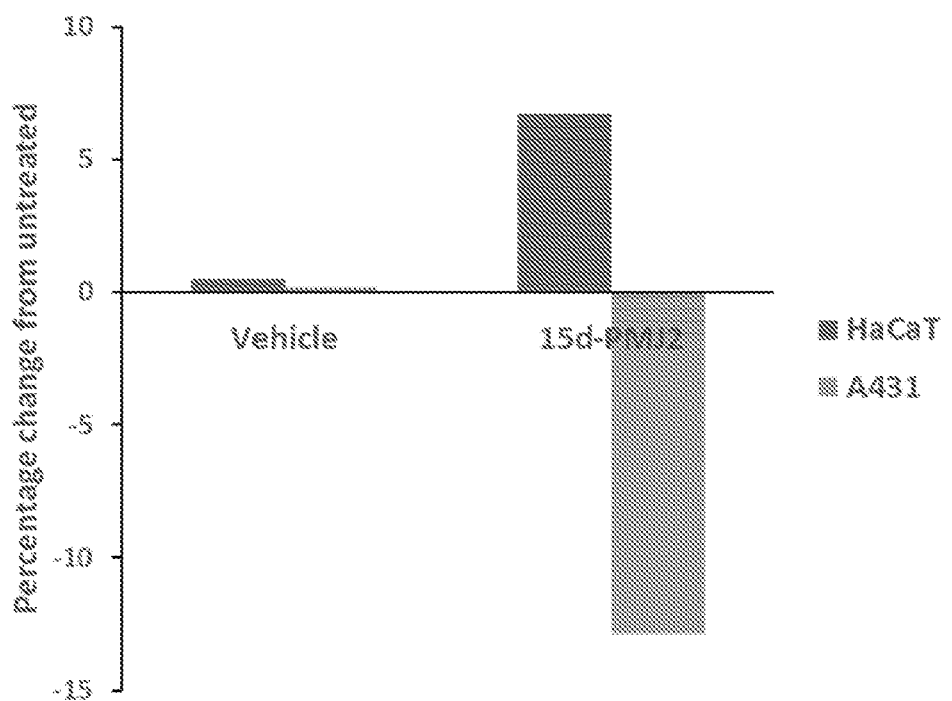
FIG. 8 is a graph showing the mean fluorescence (percentage change from untreated) for cell surface CD47 expression after exposure to vehicle or 15d-PMJ2 in either (left) human non-tumorigenic keratinocyte HaCaT cells or (right) human non-melanoma skin cancer cells A431.

Tumorigenic, A431, and non-tumorigenic, HaCaT keratinocyte cell lines were treated with 15dPMJ2 or drug vehicle (0.1% DMSO) and the cell surface expression of calreticulin (CRT; "eat me" signal) and CD47 ("don't eat me" signal) was detected by conducting flow cytometric analysis. As shown in FIGS. 7 and 8, 15dPMJ2 increased the "eat me" (CRT) signal and decreased the "don't eat me" (CD47) signal in the tumor cells; this action is expected to increase dendritic cell phagocytosis of the tumor. In contrast, 15dPMJ2 caused a slight increase in cell surface expression of CRT expression, but also an increase in the "don't eat me" signal (CD47) in non-tumor keratinocytes; this action is expected to spare the non-tumor cell from phagocytosis by dendritic cells.

Example 7

15dPMJ2-treated melanoma cells cause dendritic cell maturation.

Figure 9:
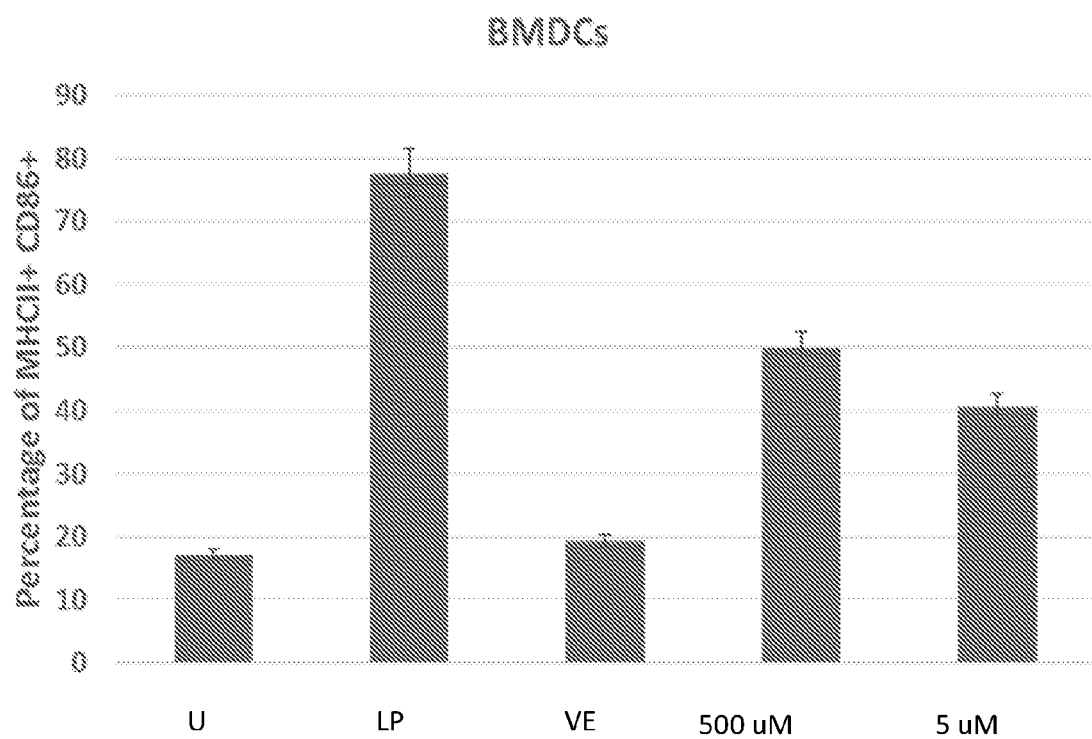
FIG. 9 is a graph showing percentage of immature dendritic cells isolated form the bone marrow of C57BL/6 mice (BMDCs) with positive fluorescence staining of activation maturation markers MHCII and CD86.

B16F10 melanoma cells remained untreated (UT) or were treated with lipopolysaccharide (LPS; positive control dendritic cell activator), vehicle (VEH; 0.1% DMSO), 500 uM oxaliplatin (OXA; positive control DAMP inducer), or 5 uM 15dPMJ2 (PMJ). The drug-treated cancer cells were then co-cultured with immature dendritic cells that were isolated from the bone marrow of C57BL/6 mice (mouse strain from which the B16F10 cell line was derived). Cell surface markers for dendritic cell maturation were then detected. As shown in FIG. 9, 15dPMJ2 significantly increased the expression of MHC II and CD86. This finding indicates that 15dPMJ2 will cause the tumor cells to be phagocytosed by dendritic cells. Oxaliplatin (OXA), which was used at 100 times the concentration of 15dPMJ2, caused similar levels of dendritic cell maturation.

Example 8

To determine if 15dPMJ$_2$ can increase the amount of tumor-attacking immune cells in melanoma tumors, a pilot xenograft study was conducted. B16F10 melanoma cells were injected into the subcutaneous flank region of C57BL/6 mice and tumor growth was allowed until tumors were palpable. Animals were then treated by the peri-tumor route with 15dPMJ$_2$, oxaliplatin (positive control DAMP inducer), cisplatin (negative control DAMP inducer), vehicle (PBS containing 0.1% DMSO) or animals were untreated. After 5 days of drug treatment, animals were euthanized and tumors excised for analysis of infiltrating immune cells (TILs). Tumors were dissociated to create a single cell suspension. The expression of MHC II and CD86 (dendritic cell maturation markers) was analyzed by conducting flow cytometric analysis.

Figure 10:
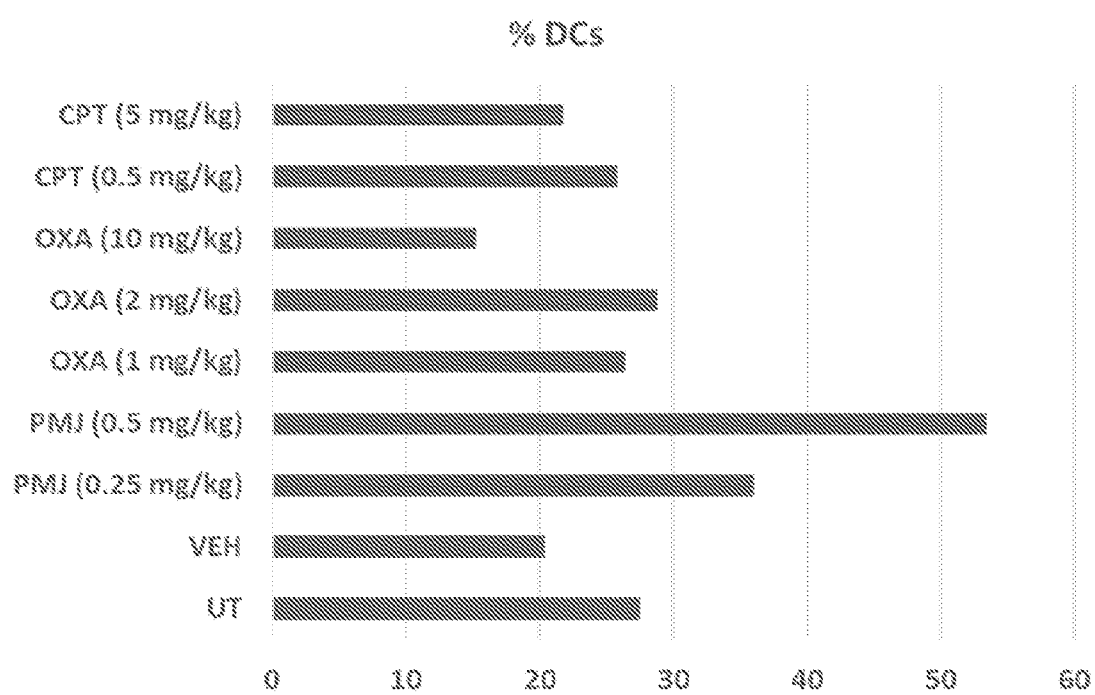
FIG. 10 is a graph showing percentage of tumor-infiltrating dendritic cells in solid melanoma tumors. Treatment groups (from top to bottom) included Cisplatin (CPT) at 5 mg/kg and 0.5 mg/kg, Oxaplatin (OXA) at 10 mg/kg, 2 mg/kg, and 1 mg/kg, 15d-PMJ2 (PMJ) at 0.5 mg/kg and 0.25 mg/kg, vehicle (VEH), and untreated (UH).

Treatment with 15dPMJ2 increased the quantity of mature dendritic cells that infiltrated the tumor compared to cisplatin (CPT)-treated, oxaliplatin (OXA)-treated, and untreated animals, as shown in FIG. 10. While not wishing to be bound to any particular theory, the presence of mature dendritic cells in the tumors indicates that dendritic cells are involved in the anti-tumor activity of 15dPMJ2.

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. An ex vivo method of activating an immune cell, the ex vivo method comprising contacting the immune cell with a compound of Formula (I):

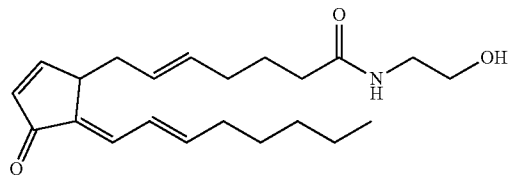

or a prodrug, derivative, and/or salt thereof to provide an engineered immune cell.

2. The ex vivo method of claim 1, wherein the prodrug has a structure of Formula (II):

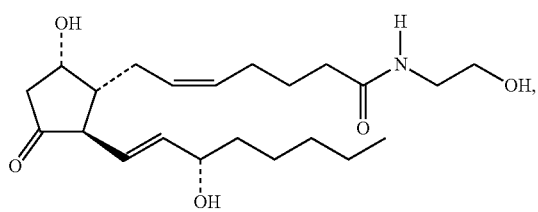

and
wherein contacting the immune cell with the compound of Formula (I) comprises contacting the immune cell with the prodrug having the structure of Formula (II).

3. The ex vivo method of claim 1, wherein the engineered immune cell is activated to attack and/or kill cancer cells and/or tumor cells.

4. The ex vivo method of claim 1, wherein the method induces maturation of the immune cell.

5. The ex vivo method of claim 1, wherein the immune cell is a dendritic cell and the dendritic cell is activated to uptake, process, and/or present pathogen-derived or host-derived antigenic peptides to naive T-cells.

6. The ex vivo method of claim 1, wherein the immune cell is a T-cell and the method activates the T-cell to produce a multivalent cellular immune response against a given antigen.

7. The ex vivo method of claim 3, wherein the cancer cells and/or tumor cells are drug resistant cells, metastatic tumor cells, and/or tumor stem cells.

8. An ex vivo method of activating an immune cell, the ex vivo method comprising:
contacting a cancer cell with a compound of Formula (I):

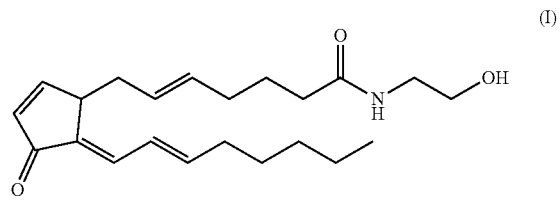 [SMILES: CCCCC/C=C/C=C1/C(=O)C=CC1C/C=C/CCCC(=O)NCCO]

or a prodrug, derivative, and/or salt thereof to provide a drug-treated cancer cell; and
co-culturing the drug-treated cancer cell and an immune cell to provide an activated immune cell.

9. The ex vivo method of claim 1, wherein the engineered immune cell is not activated to attack and/or kill non-cancer cells and/or non-tumor cells.

10. The ex vivo method of claim 6, wherein the multivalent cellular immune response is greater than a response achieved with the given antigen alone.

11. The ex vivo method of claim 1, further comprising administering the engineered immune cell to a subject.

12. The ex vivo method of claim 1, further comprising culturing the engineered immune cell.

13. The ex vivo method of claim 8, wherein the prodrug has a structure of Formula (II):

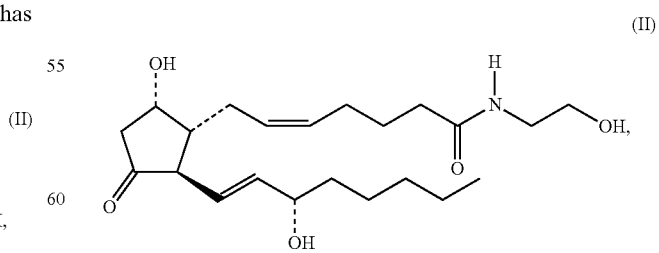

and
wherein contacting the cancer cell with the compound of Formula (I) comprises contacting the cancer cell with the prodrug having the structure of Formula (II).

14. The ex vivo method of claim 8, wherein the activated immune cell is activated to attack and/or kill cancer cells and/or tumor cells.

15. The ex vivo method of claim 8, wherein the method induces maturation of the immune cell.

16. The ex vivo method of claim 8, wherein the immune cell is a dendritic cell and the dendritic cell is activated to uptake, process, and/or present pathogen- derived or host-derived antigenic peptides to naive T-cells.

17. The ex vivo method of claim 8, wherein the immune cell is a T-cell and the method activates the T-cell to produce a multivalent cellular immune response against a given antigen.

18. The ex vivo method of claim 17, wherein the multivalent cellular immune response is greater than a response achieved with the given antigen alone.

19. The ex vivo method of claim 14, wherein the cancer cells and/or tumor cells are drug resistant cells, metastatic tumor cells, and/or tumor stem cells.

20. The ex vivo method of claim 8, further comprising administering the activated immune cell to a subject.

\* \* \* \* \*